United States Patent
Romano

[11] Patent Number: 5,874,742
[45] Date of Patent: Feb. 23, 1999

[54] COUNTERFEIT DETECTION VIEWER APPARATUS FOR PAPER CURRENCY

[76] Inventor: Camille Romano, 7436 SW. 117th Ave. Suite 208, Miami, Fla. 33183

[21] Appl. No.: 772,811

[22] Filed: Dec. 24, 1996

[51] Int. Cl.[6] .................................................. G01N 21/64
[52] U.S. Cl. ..................................... 250/461.1; 250/458.1; 250/504 H
[58] Field of Search ............................. 250/458.1, 461.1, 250/485.1, 504 R, 504 H

[56] References Cited

U.S. PATENT DOCUMENTS

| | | | |
|---|---|---|---|
| 3,618,765 | 11/1971 | Cooper et al. | 209/122 |
| 3,774,046 | 11/1973 | Hoch et al. | 250/485 |
| 3,842,281 | 10/1974 | Goodrich | 250/461 |
| 4,558,224 | 12/1985 | Gober | 250/461.1 |
| 4,634,872 | 1/1987 | Janus et al. | 250/458.1 |
| 5,444,263 | 8/1995 | Mastnak | 250/504 H |
| 5,572,319 | 11/1996 | Blackman et al. | 250/485.1 |
| 5,640,463 | 6/1997 | Csultis | 382/135 |
| 5,668,377 | 9/1997 | Erickson | 250/504 R |

FOREIGN PATENT DOCUMENTS

| | | | |
|---|---|---|---|
| 63-298140 | 12/1988 | Japan | 250/485.1 |

*Primary Examiner*—Edward J. Glick
*Assistant Examiner*—Darren M. Jiron
*Attorney, Agent, or Firm*—Ezra Sutton

[57] ABSTRACT

A counterfeit detection viewer apparatus for detecting security markings in paper currency, which includes a housing having a detection opening on the bottom thereof for receiving the paper currency to be inspected and a viewing opening on the top thereof for inspecting the paper currency. A UV light fixture is mounted in the housing and has a UV fluorescent lamp for projecting UV light rays toward the detection opening and the paper currency to be inspected. The UV light fixture includes a reflector to reflect the UV light rays toward the detection opening and the paper currency, and a switch for activating the UV fluorescent lamp prior to inspecting the paper currency through the viewing opening.

11 Claims, 5 Drawing Sheets

COUNTERFEIT DETECTION VIEWER APPARATUS FOR PAPER CURRENCY

FIELD OF THE INVENTION

This invention relates to an improved counterfeit detection viewer apparatus for the detection of counterfeit paper currency. More particularly, it relates to an apparatus for identifying instantaneously the security markings of valid paper currency by using ultra violet fluorescent lighting.

BACKGROUND OF THE INVENTION

It is well known that ever since paper currency was developed and put into use, the governments throughout the world have been concerned with the problem of counterfeiting. As duplicating and printing, and especially color photocopying techniques have advanced over the years, it is more difficult than ever to distinguish between counterfeit and legitimate paper currency. It is obvious that the problem of counterfeiting paper currency is and has been a major concern of many governments, banks, commercial businesses and retail stores around the world.

In response to the challenge of the ever growing concern of counterfeiting, various instruments and detectors have been developed for detecting counterfeit currency. However, it has been discovered that known instruments and detectors are not reliable, or are too expensive to manufacture. In some cases such instruments are too bulky and/or complex in design.

In addition, recently new U.S. currency has been developed to include new security features including a polymer thread which has fluorescent markings sensitive to ultra violet light and which are barely visible in ambient lighting conditions. However, under intensified ultra violet fluorescent lighting, the polymer thread glows red to indicate that the currency is authentic.

There remains a need for a counterfeit detection viewer apparatus that instantaneously authenticates and validates the security markings of U.S. paper currency, foreign currency and essential governmental documents. In addition, the counterfeit detection view apparatus should be portable, lightweight, durable, battery-operated and convenient to use. Also, the apparatus should provide a counterfeit detection system and methodology for the duplicate checking of counterfeit currency or governmental documents.

DESCRIPTION OF THE PRIOR ART

Counterfeit detection instruments, counterfeit detection apparatus and the like having various designs, structure, configurations and materials of construction have been disclosed in the prior art. For example, U.S. Pat. No. 3,618,765 to Cooper et al discloses a counterfeit currency detector having a housing and light sources. The light sources are long-wave ultraviolet light bulbs with an integral filter or exterior filter to absorb most visible light and transmit the desired ultraviolet rays. The light sources are located in the upper surface area of the housing, which has an opening to facilitate positioning of the paper currency below the filter, such that the currency is exposed to the UV light sources. This prior art patent does not disclose the design, structure and configuration of the present invention.

U.S. Pat. Nos. 3,725,694; 3,774,046; and 4,558,224 all disclose counterfeit currency detectors having a housing unit and a UV light source with an internal bill receptor for exposing the bill to the UV light source. None of these aforementioned prior art patents disclose the design, structure and configuration of the present invention.

These prior art patents do not disclose or teach the use of an instrument for instantaneous detection of counterfeit currency or false documents having the design and configuration of the present invention.

Accordingly, it is an object of the present invention to provide a counterfeit detection viewer apparatus that allows for instantaneous detection of security markings of valid and authentic paper currency, or showing the lack of proper security markings of counterfeit paper currency.

Another object of the present invention is to provide a counterfeit detection viewer apparatus for instantly detecting the security markings and verifying the validity and authenticity of any essential documents that include passports, entry visas, immigration green cards, driving licenses, vehicle registrations, credit cards, travelers checks, or other foreign currencies.

Another object of the present invention is to provide a counterfeit detection viewer apparatus for instantly detecting counterfeit paper currency by providing a housing to intensify UV fluorescent light from a fluorescent lamp, even under normal ambient bright lighting conditions.

Another object of the present invention is to provide a counterfeit detection viewer apparatus that is easy to use, portable, convenient and durable.

Another object of the present invention is to provide a counterfeit detection viewer apparatus that is portable, battery-operated, lightweight, compact and hand held.

Another object of the present invention is to provide a counterfeit detection viewer apparatus having exterior storage compartments for pen-type chemical markers that include a counterfeit chemical detector for detecting counterfeit paper currency and a fluorescent marker for identification of valuables under UV lighting.

Another object of the present invention is to provide a counterfeit detection viewer apparatus that can be mass produced in an automated and economical manner and is readily affordable by the user.

SUMMARY OF THE INVENTION

In accordance with the present invention, there is provided a counterfeit detection viewer apparatus for detecting security markings in paper currency, which includes a housing having a detection opening on the bottom thereof for receiving the paper currency to be inspected and a viewing opening on the top thereof for inspecting the paper currency. A UV light fixture is mounted in the housing and has a UV fluorescent lamp for projecting UV light rays toward the detection opening and the paper currency to be inspected. The UV light fixture includes a reflector to reflect the UV light rays toward the detection opening and the paper currency.

BRIEF DESCRIPTION OF THE DRAWINGS

Further objects, features, and advantages of the present invention will become apparent upon consideration of the detailed description of the presently-preferred embodiments, when taken in conjunction with the accompanying drawings wherein.

DETAILED DESCRIPTION OF THE PREFERRED AND ALTERNATE EMBODIMENTS

OVERVIEW

Figure 1:
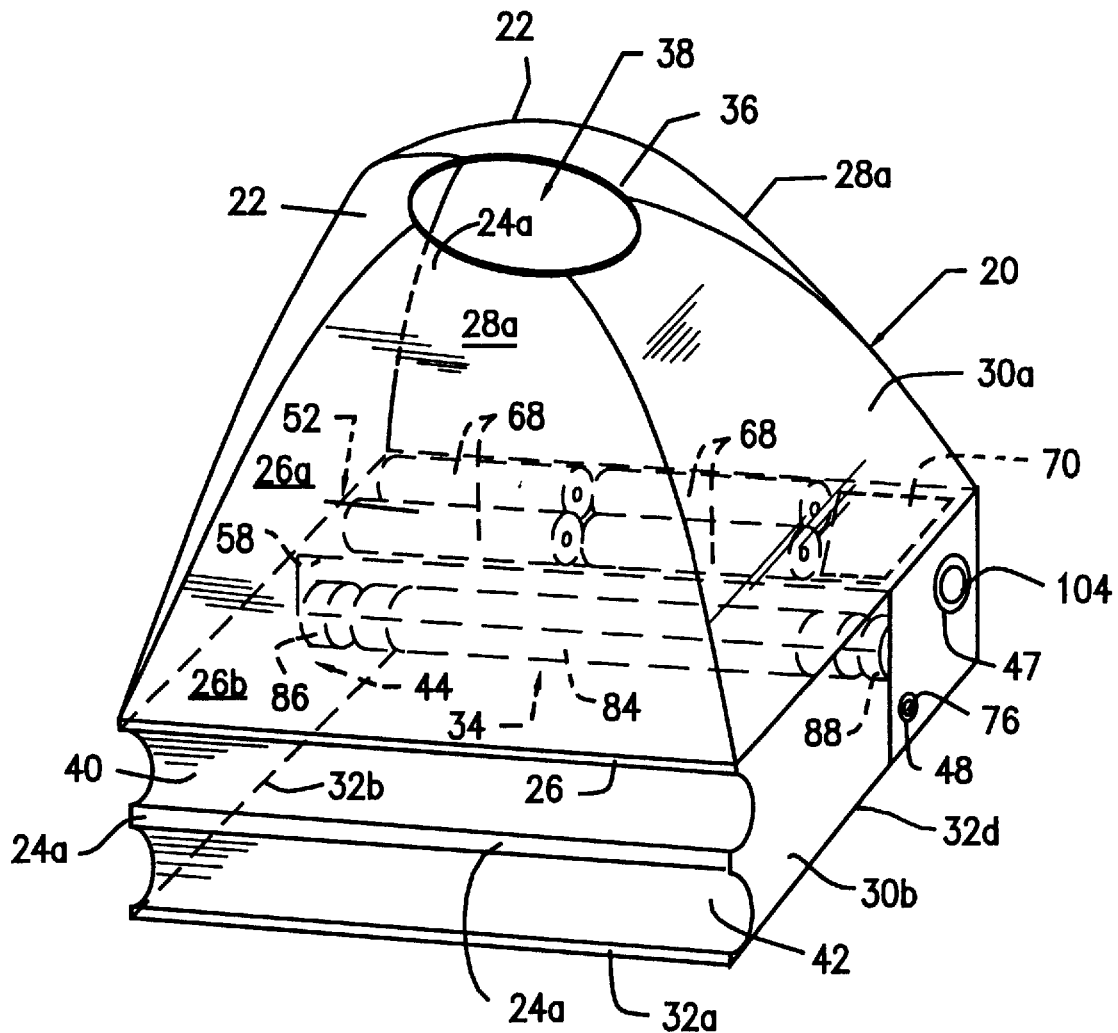
FIG. 1 is a front perspective view of the counterfeit detection viewer apparatus of the preferred embodiment of the present invention showing the major component parts contained therein.
Figure 2:
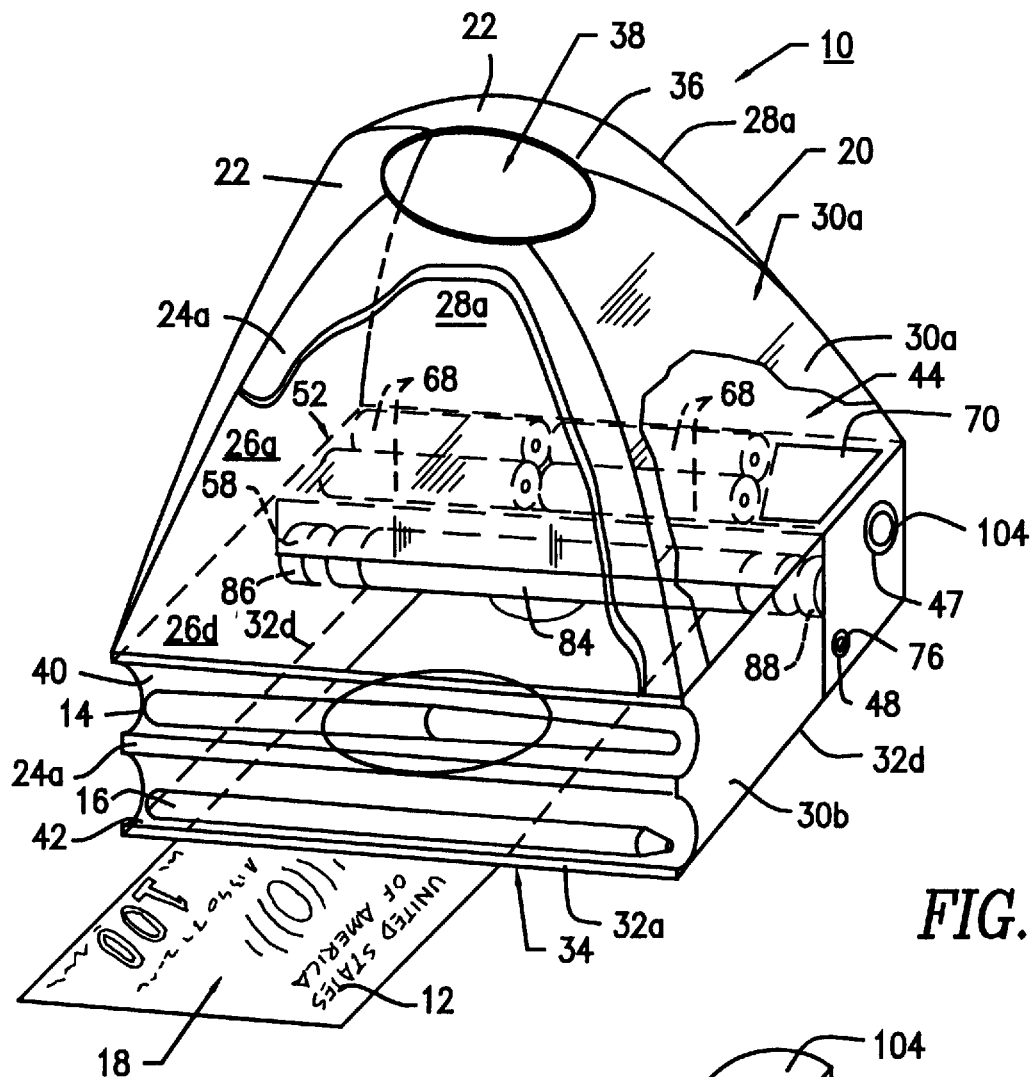
FIG. 2 is a front perspective view of the counterfeit detection viewer apparatus of the preferred embodiment of the present invention showing the major component parts contained therein and in operational use.
Figure 2A:
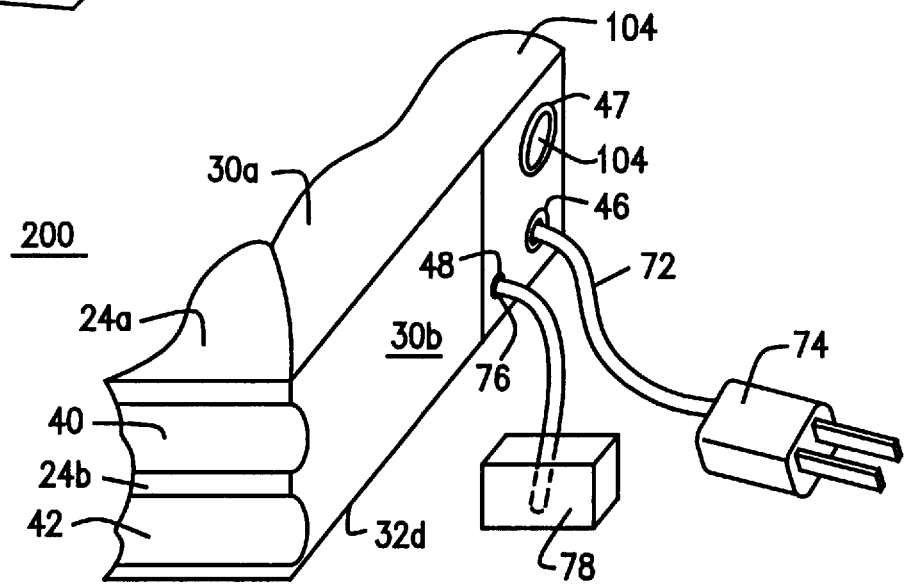
FIG. 2A is a perspective view of the counterfeit detection viewer apparatus of the alternate embodiment of the present invention showing the ON/OFF button, the AC adaptor connector, and the electrical cord and plug for an AC connection.

The counterfeit detection viewer apparatus 10 and its component parts of the preferred and alternate embodiments of the present invention are represented in detail by FIGS. 1 through 6 of the drawings. The counterfeit detection viewer apparatus 10 of the preferred embodiment, as shown in FIGS. 1 and 2, is a portable unit used for the detection of counterfeit paper currency 12 and is operated by batteries 68. The counterfeit detection viewer apparatus 200 of the alternate embodiment, as shown in FIG. 2A, is a stationary unit having a standard electrical cord 72 and an AC three-prong plug 74 and is operated by a standard AC 115 V electrical outlet 106. In all other respects, the counterfeit detection viewer apparatus 200 of the alternate embodiment functions and operates in the same manner as the counterfeit detection viewer apparatus 10 of the preferred embodiment.

PREFERRED EMBODIMENT 10

The counterfeit detection viewer apparatus 10 and its component parts of the preferred embodiment of the present invention are represented in detail by FIGS. 1 to 6. The counterfeit detection viewer apparatus 10 includes a housing 20 having a domed configuration, and an internal UV lighting assembly 50 having a battery compartment 62 for batteries 68 and a UV lighting fixture 82 using a UV fluorescent tube 84 for detecting the security marking 18 of an authentic paper currency 12. As shown in FIG. 2, the counterfeit detection viewer apparatus 10 is in an operational mode for detecting the security marking 18 in order to detect a counterfeit currency bill from a valid and authentic currency bill.

Figure 3:
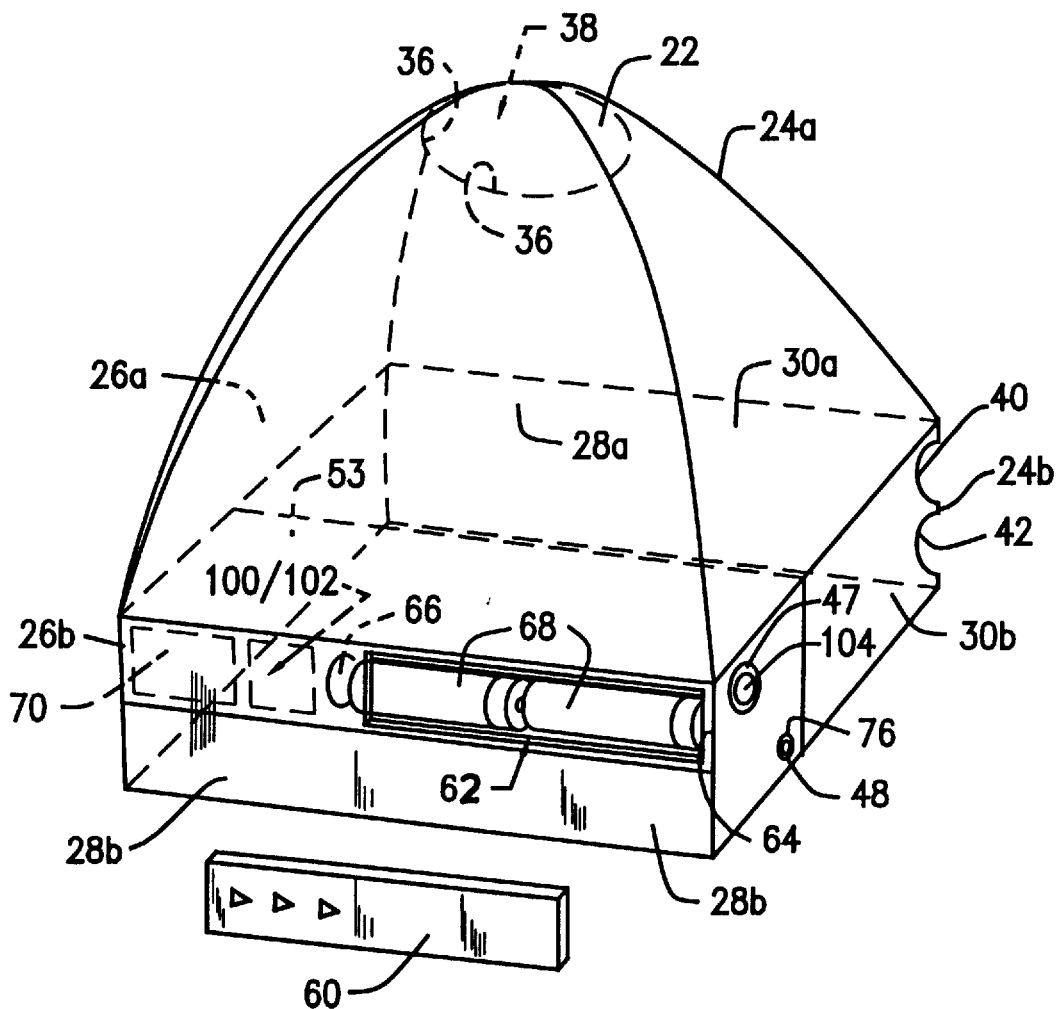
FIG. 3 is a rear perspective view of the counterfeit detection viewer apparatus of the preferred embodiment of the present invention showing the battery compartment, ON/OFF button, batteries, and viewing opening.
Figure 4:
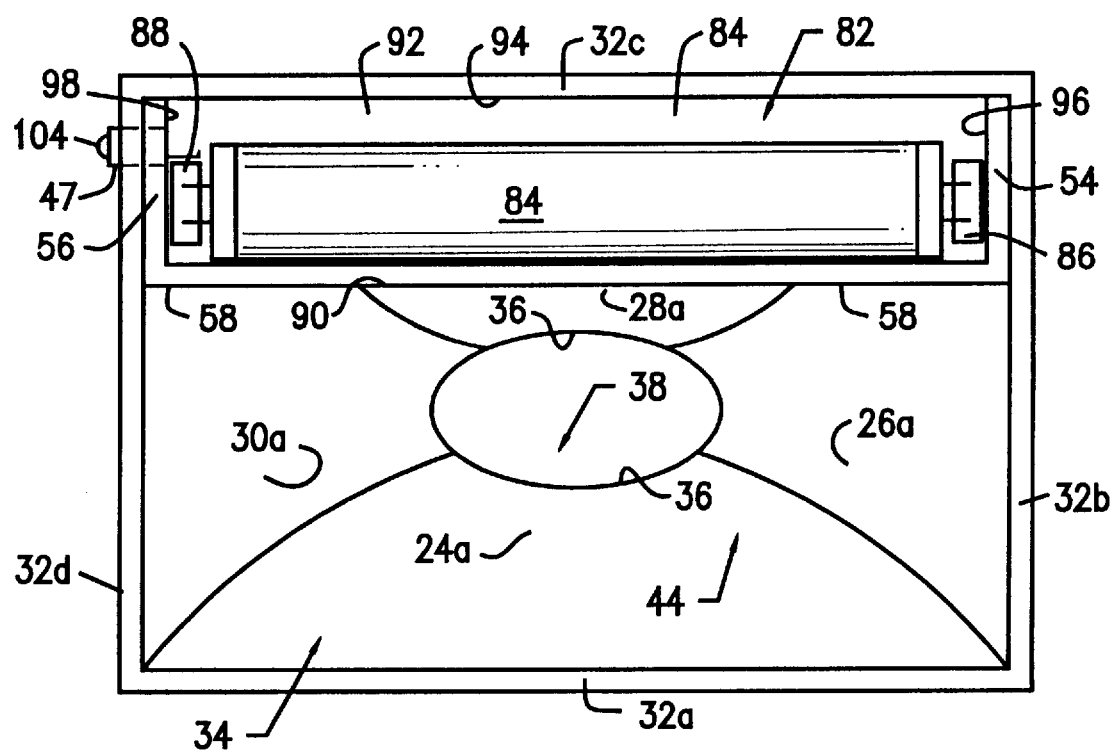
FIG. 4 is a bottom plan view of the counterfeit detection viewer apparatus of the preferred embodiment of the present invention showing the detection opening, the viewing opening, and the UV fluorescent tube with miniature sockets.
Figure 5:
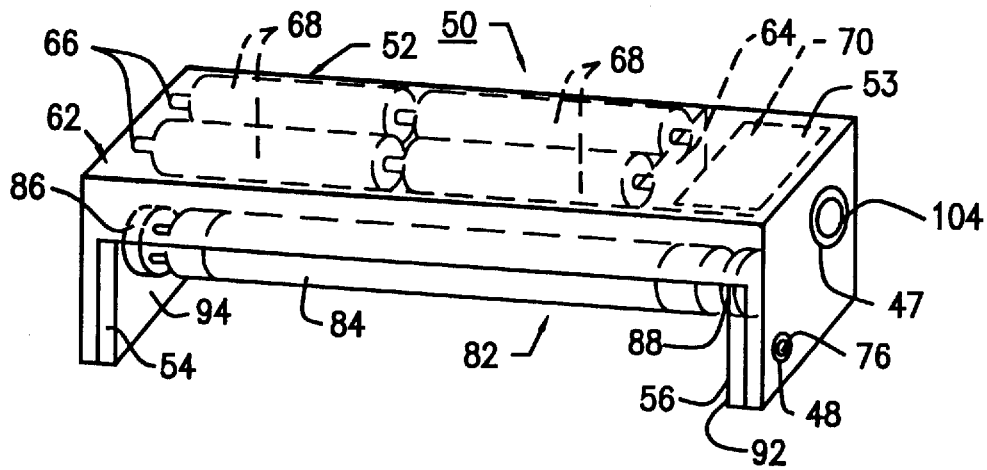
FIG. 5 is a front perspective view of the counterfeit detection viewer apparatus of the present invention showing the internal UV lighting component and the major component parts contained therein.

Housing unit 20 has a top wall section 22, upper sidewalls 24a, 26a, 28a, and 30a, and lower sidewalls 24b, 26b, 28b and 30b, all being integrally connected to form a substantially square-shaped dome configuration which forms an interior compartment 44. As shown in FIG. 3, housing unit 20 further includes bottom perimeter edges 32a, 32b, 32c and 32d which defines a detection opening 34 on the bottom of housing 20, and includes an upper oval perimeter edging 36 which defines a viewer opening 38 at the top of housing 20. Front lower sidewall 24b includes a pair of exterior upper and lower holding compartments 40 and 42 in the configuration of U-shaped grooved channels for receiving and holding a counterfeit chemical detection pen 14 and a fluorescent marker pen 16, respectively. These pens 14 and 16 are used in conjunction with the counterfeit detection viewer apparatus 10 to form a complete detection system for authenticating currency 12 and governmental documents. Lower sidewall 30b includes a first circular hole opening 47 for an ON/OFF button 104 and a second circular hole opening 48 for an AC electrical wire connector 76 being used in conjunction with an AC adaptor connector 78, as shown in FIG. 2A.

The exterior surface of housing unit 20 is coated with a metallic silver layer of material and the interior surface of internal compartment 44 is coated with a dark layer of material (for example, black) which provides a better contrast of illumination to the viewer when the UV fluorescent tube 84 is turned on and is in operational use. The housing unit 20 preferably has a width and depth of 13 cm each and a height of 13 cm. The oval viewing opening 38 preferably has a width of 3 cm and a length of 8 cm. Housing unit 20 can be made of a moldable, and durable plastic or a lightweight metal material.

As shown in FIGS. 1 to 6, the internal UV lighting assembly 50 includes a fixture housing 52 having an interior top wall 53, side walls 54 and 56, a partial front wall 58 and a slidable battery cover 60 being located on the rear side wall 28b. The internal UV lighting assembly 50 further includes an internal battery compartment 62 having a positive pole (+) member 64 and a negative pole (−) member 66 for holding a plurality of batteries 68. Battery compartment 62 also includes an AC electrical adaptor component 70 being adjacent to the aforementioned battery compartment 62, as depicted in FIGS. 1 and 2 of the drawings.

In addition, the internal UV lighting assembly 50 also includes a UV lighting fixture 82 having a UV fluorescent tube 84 which is received within miniature sockets 86 and 88. The UV lighting fixture 82 includes interior wall surfaces 90, 92, 94, 96, and 98 for reflecting and intensifying the UV light 110 from the UV fluorescent tube 84 to provide easier identification and reading of the security marking 18 on a currency bill 12. At least one of the walls is coated to have a mirror-like finish to increase reflectivity. The reflecting interior walls 90, 92, 94, 96 and 98 can be made of silverized plastic, polished metal, a reflective metallic finish or a painted reflective finish. UV fluorescent tube 84 has a length in the range of 6 cms to 18 cms with a preferred length of 11 cms. Also, the UV fluorescent tube 84 has a power rating specification in the range of 2 watts to 6 watts with a preferred power rating of 3 watts.

The distance between the UV fluorescent tube 84 and the currency bill 12 being scanned should not be more than 0.5 centimeters (cm), as this small distance between the UV fluorescent tube 84 and bill 12 also provides a more intense illumination of the security marking 18 being scanned. For example, new U.S. dollar bills 12 (all denominations) have a security thread marking 18 which glows red under the intense illumination provided by the UV fluorescent tube 84 of the TV lighting fixture 82 of the viewer apparatus 10. Currency bill 12 (for example the U.S. $100 bill) not having the red glow of the security thread marking 18 would indicate that currency bill 12 being tested is a counterfeit. The user could also do a duplicate check by using the counterfeit chemical detection pen 14 from compartment 40 which would also show the authenticity or the invalidity of the currency bill 12 being tested by the user.

Figure 6:
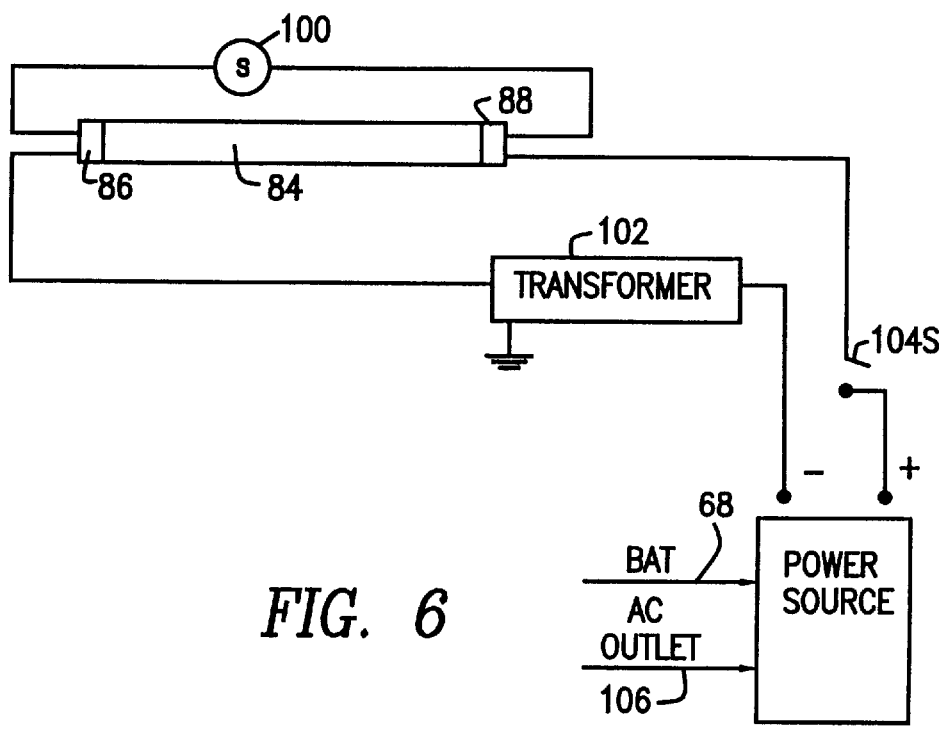
FIG. 6 is an electrical schematic diagram of the counterfeit detection viewer apparatus of the present invention showing the electrical circuit.

In addition, viewer apparatus 10 uses a UV starter 100 and a UV transformer 102 to light-up the UV fluorescent tube 84 via ON/OFF button 104, as shown in FIG. 6.

ALTERNATE EMBODIMENT 200

Counterfeit detection viewer apparatus 200 of the alternate embodiment of the present invention is depicted in FIG. 2A. All aspects of viewer apparatus 200 of the alternate embodiment are the same as the counterfeit viewer apparatus 10 of the preferred embodiment, except for the additional circular hole opening 46 on lower sidewall 30b which is used for receiving an electrical cord 72 with an AC three-prong plug 74. In addition, viewer apparatus 200 is powered by a standard AC 115 V electrical outlet 106 via plug 74. As shown in FIG. 6, viewer apparatus 200 uses a UV starter 100 and a UV transformer 102 in which to light-up the UV fluorescent tube 84 via the ON/OFF switch 104.

OPERATION OF THE PRESENT INVENTION

In operation, the user places the detection opening 34 of the counterfeit detection viewer apparatus 10 over the paper currency bill 12 to be inspected and scanned, as depicted in detail by FIG. 2. For example, new U.S. currency has a polymer thread with florescent markings sensitive to UV fluorescent light, and which will glow red under intense UV fluorescent illumination. The user then depresses the ON/OFF button 104 to the ON position which in turn activates and illuminates the UV fluorescent tube 84 via the power source of batteries 68 of the UV lighting assembly 50. The user then peers into the viewer opening 38 in order to determine the validity and authenticity of the currency bill 12 being scrutinized. The viewer will instantly see if a security marking 18 is present on the bill 12 being scanned as is it will glow red, and if there is no security marking 18 on the bill 12 being scanned, then the bill 12 is determined to be a counterfeit. An additional check can be used to determine authenticity or invalidity of bill 12 by the use of the counterfeit chemical detection pen 14. The use of the viewer apparatus 10 and detection pen 14 provides an effective counterfeit detection system for determining if paper currency 12 is counterfeit. When the user has finished operating the counterfeit detection apparatus 10, the user simply depresses again the ON/OFF button 104 to shut off the viewer apparatus 10. This conserves and saves the life of the batteries 68 being used to energize the viewer apparatus 10.

In operating the counterfeit detection viewer apparatus 200 of the alternate embodiment, the user simply plugs in the three-prong plug 74 into an AC electrical outlet 106 for energizing the viewer apparatus 200 and switches ON the ON/OFF switch 104S. In all other respects the viewer apparatus 200 functions and operates in the same manner as the counterfeit detection viewer apparatus 10 of the preferred embodiment.

ADVANTAGES OF THE PRESENT INVENTION

Accordingly, an advantage of the present invention is that it provides for a counterfeit detection viewer apparatus that allows for instantaneous detection of security markings of valid and authentic paper currency, or showing the lack of proper security markings of a counterfeit paper currency.

Another advantage of the present invention is that it provides for a counterfeit detection viewer apparatus for instantly detecting the security markings and verifying the validity and authenticity of any essential documents that include passports, entry visas, immigration green cards, driving licenses, vehicle registrations, credit cards, travelers checks, or other foreign currencies.

Another advantage of the present invention is that it provides for a counterfeit detection viewer apparatus for instantly detecting counterfeit paper currency by providing a housing to intensify UV fluorescent light rays from a fluorescent lamp, even under normal ambient bright lighting conditions.

Another advantage of the present invention is that it provides for a counterfeit detection viewer apparatus that is easy to use, portable, convenient and durable.

Another advantage of the present invention is that it provides for a counterfeit detection viewer apparatus that is portable, battery-operated, lightweight, compact and hand held.

Another advantage of the present invention is that it provides for a counterfeit detection viewer apparatus having exterior storage compartments for pen-type chemical markers that include a counterfeit chemical detector for detecting counterfeit paper currency and a fluorescent marker for identification of valuables under UV lighting.

Another advantage of the present invention is that it provides for a counterfeit detection viewer apparatus that can be mass produced in an automated and economical manner and is readily affordable by the user.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A counterfeit detection viewer apparatus for detecting security markings in paper currency, comprising:

a) a housing having a detection opening on the bottom thereof for receiving the paper currency to be inspected and a viewing opening on the top thereof for inspecting the paper currency; the interior of said housing having a dark coating;

b) a UV light fixture mounted in said housing having a UV fluorescent lamp for projecting UV light rays toward said detection opening and the paper currency to be inspected; said UV fluorescent lamp is not more than 0.5 centimeters from said detection opening; and c) means for activating said UV fluorescent lamp prior to inspecting the paper currency through said viewing opening.

2. A counterfeit detection viewer apparatus in accordance with claim 1, further including reflector means mounted within said UV light fixture to reflect said UV light rays toward said detection opening, and wherein said reflector means is made of silverized plastic, polished metal, a reflective metallic finish or a painted reflective finish.

3. A counterfeit detection viewer apparatus in accordance with claim 2, wherein said reflector means has a U-shaped configuration.

4. A counterfeit detection viewer apparatus in accordance with claim 1, wherein said means for activating includes a switch located on said housing.

5. A counterfeit detection viewer apparatus in accordance with claim 4, wherein said means for activating said UV fluorescent lamp includes a battery compartment having a plurality of batteries for generating electrical current.

6. A counterfeit detection viewer apparatus in accordance with claim 4, wherein said means for activating said UV fluorescent lamp includes an electrical cord and plug for receiving electrical current.

7. A counterfeit detection viewer apparatus in accordance with claim 1, wherein said housing has an exterior wall, said exterior wall having recesses formed therein for receiving counterfeit detector pens.

8. A counterfeit detection viewer apparatus in accordance with claim 1, wherein said housing is made of a plastic or a lightweight metal.

9. A counterfeit detection viewer apparatus in accordance with claim 1, wherein said UV fluorescent lamp has a length in the range of 6 cms to 18 cms.

10. A counterfeit detection viewer apparatus in accordance with claim 1, wherein said UV fluorescent lamp has a power rating specification in the range of 2 watts to 6 watts.

11. A counterfeit detection viewer apparatus for detecting security markings in paper currency, comprising:

a) a housing having a detection opening on the bottom thereof for receiving the paper currency to be inspected and a viewing opening on the top thereof for inspecting the paper currency; the interior of said housing having a dark coating;

b) a UV light fixture mounted in said housing having a UV fluorescent lamp for projecting UV light rays toward said detection opening and the paper currency to be inspected; said UV fluorescent lamp is not more than 0.5 centimeters from said detection opening; and c) means for activating said UV fluorescent lamp prior to inspecting the paper currency through said viewing opening; and d) wherein said housing has an exterior wall, said exterior wall having recesses formed therein for receiving counterfeit detector pens.

\* \* \* \* \*